United States Patent
Breivik (10) Patent No.: US 11,367,237 B2
(45) Date of Patent: Jun. 21, 2022

(54) METHOD AND SYSTEM FOR CONTROLLING A VIRTUAL LIGHT SOURCE FOR VOLUME-RENDERED IMAGES

(71) Applicant: GE Precision Healthcare LLC, Wauwatosa, WI (US)

(72) Inventor: Lars Hofsoy Breivik, Oslo (NO)

(73) Assignee: GE Precision Healthcare LLC, Wauwatosa, WI (US)

( * ) Notice: Subject to any disclaimer, the term of this patent is extended or adjusted under 35 U.S.C. 154(b) by 86 days.

(21) Appl. No.: 16/918,226

(22) Filed: Jul. 1, 2020

(65) Prior Publication Data

US 2022/0005252 A1 Jan. 6, 2022

(51) Int. Cl.
| | |
|---|---|
| *G06T 15/00* | (2011.01) |
| *G06T 15/08* | (2011.01) |
| *A61B 8/08* | (2006.01) |
| *A61B 8/00* | (2006.01) |

(52) U.S. Cl.
CPC .......... *G06T 15/005* (2013.01); *A61B 8/466* (2013.01); *A61B 8/467* (2013.01); *A61B 8/483* (2013.01); *A61B 8/54* (2013.01); *G06T 15/08* (2013.01); *G06T 2200/24* (2013.01); *G06T 2210/41* (2013.01)

(58) Field of Classification Search
None
See application file for complete search history.

(56) References Cited

U.S. PATENT DOCUMENTS

| | | | | |
|---|---|---|---|---|
| 2004/0081340 | A1* | 4/2004 | Hashimoto | G01S 7/52036 382/128 |
| 2019/0147645 | A1* | 5/2019 | Mory | G06T 15/50 600/443 |

* cited by examiner

*Primary Examiner* — Tapas Mazumder (57) ABSTRACT

A system and method for controlling a virtual light source includes generating a volume-rendered image including a rendered object, controlling a shading and an illumination of the volume-rendered image based on a position of the virtual light source with respect to the rendered object, and receiving a control input from a user interface. The system and method includes automatically moving the virtual light source to an updated position along a height contour established with respect to a surface of a rendered object in the volume-rendered image in response to the control input. The system and method includes calculating an updated shading and an updated illumination based on the updated virtual light source position.

20 Claims, 8 Drawing Sheets

METHOD AND SYSTEM FOR CONTROLLING A VIRTUAL LIGHT SOURCE FOR VOLUME-RENDERED IMAGES

FIELD OF THE INVENTION

This disclosure relates generally to a method and system for controlling a position of a virtual light source when displaying a volume-rendered image.

BACKGROUND OF THE INVENTION

Volume-rendered images are very useful for representing 3D medical imaging datasets. Volume-rendered images are typically 2D representations of a 3D medical imaging dataset. There are currently many different techniques for generating a volume-rendered image. One such technique, raycasting, includes projecting a number of rays through the 3D medical imaging dataset. Each sample in the 3D medical imaging dataset is mapped to a color and a transparency. Data is accumulated along each of the rays. According to one common technique, the accumulated data along each of the rays is displayed as a pixel in the volume-rendered image. In order to gain an additional sense of depth and perspective, volume-rendered images are oftentimes shaded and illuminated based on the position of a virtual light source with respect to the rendered object shown in the volume-rendered image. Shading and illumination may be used in order to help convey the relative positioning of structures or surfaces shown in the volume-rendered image. The shading and illumination helps a viewer to more easily visualize the three-dimensional shape of the rendered object represented in the volume-rendered image.

In order to fully understand the three-dimensional shape of the rendered object in the volume-rendered image, it may be desired for the user to adjust the position of the virtual light source used to calculate the shading and illumination of the volume-rendered image. Viewing the volume-rendered while it is illuminated and shaded with the virtual light source in different positions will help the user to more fully understand the three-dimensional shape and geometry of the rendered object in the volume-rendered image.

Conventional solutions are configured to adjust the angular position of a virtual light source with respect to the rendered object. However, depending on the shape of the rendered object represented in the volume-rendering, this oftentimes results in different distances between the virtual light source and the rendered object. Conventional volume-rendering techniques typically model the intensity of light from the light source to decrease with distance. This results in lower levels of illumination when the virtual light source is a greater distance from the rendered object.

According to other conventional solutions, the user needs to control the position of the virtual light source or sources in three-dimensional space. It can be difficult for the user to quickly and accurately position the virtual light source in the desired position due to the challenges of controlling the three-dimensional position of the virtual light source with respect to the rendered object.

Therefore, for these and other reasons, an improved system and method for controlling the position of a virtual light source is desired.

BRIEF DESCRIPTION OF THE INVENTION

The above-mentioned shortcomings, disadvantages and problems are addressed herein which will be understood by reading and understanding the following specification.

In an embodiment, a method of volume-rendering includes accessing a 3D medical imaging dataset and generating a volume-rendered image including a rendered object from the 3D medical imaging dataset. The method includes controlling a shading and an illumination of the volume-rendered image based on a position of a virtual light source with respect to the rendered object. Controlling the shading and the illumination includes performing the following steps: a) receiving a control input from a user interface; b) automatically moving the virtual light source to an updated position along a height contour established with respect to a surface of a rendered object in the volume-rendered image in response to the control input; c) calculating an updated shading and an updated illumination based on the updated virtual light source position; d) displaying the volume-rendered image with the updated shading and the updated illumination; and e) repeating steps a), b), c), and d), as the virtual light source is being moved in response to the control input.

In an embodiment, a system for interacting with a 3D medical imaging dataset includes a display device, a user interface, and a processor communicatively connected to the display device and the user interface. The processor is configured to access the 3D medical imaging dataset and generate a volume-rendered image including a medical object from the 3D medical imaging dataset. The processor is configured to receive a control input from the user interface to adjust a position of a virtual light source with respect to the rendered object, wherein the position of the virtual light source is used to calculate an illumination and a shading of the volume-rendered image. The processor is configured to automatically move the virtual light source to an updated position along a height contour established with respect to the surface of a rendered object in the volume-rendered image in response to the control input. The processor is configured to display the volume-rendered image with the illumination and the shading determined based on a real-time position of the virtual light source during the process of automatically moving the virtual light source to the updated position.

In an embodiment, an ultrasound imaging system includes an ultrasound probe, a display device, a memory, a user interface, and a processor communicatively connected to the ultrasound probe, the display device, the memory, and the user interface. The processor is configured to control the ultrasound probe to acquire a 3D ultrasound dataset and generate a volume-rendered image including a rendered object from the 3D ultrasound dataset. The processor is configured to receive a control input from the user interface to adjust a position of a virtual light source with respect to the rendered object, wherein the position of the virtual light source is used to calculate an illumination and a shading of the volume-rendered image. The processor is configured to automatically move the virtual light source to an updated position along a height contour established with respect to a surface of a rendered object in the volume-rendered image in response to the control input. The processor is configured to display the volume-rendered image with the illumination and the shading determined based on a real-time position of the virtual light source during the process of automatically moving the virtual light source to the updated position.

Various other features, objects, and advantages of the invention will be made apparent to those skilled in the art from the accompanying drawings and detailed description thereof.

DETAILED DESCRIPTION OF THE INVENTION

In the following detailed description, reference is made to the accompanying drawings that form a part hereof, and in which is shown by way of illustration specific embodiments that may be practiced. These embodiments are described in sufficient detail to enable those skilled in the art to practice the embodiments, and it is to be understood that other embodiments may be utilized and that logical, mechanical, electrical and other changes may be made without departing from the scope of the embodiments. The following detailed description is, therefore, not to be taken as limiting the scope of the invention.

Figure 1A:
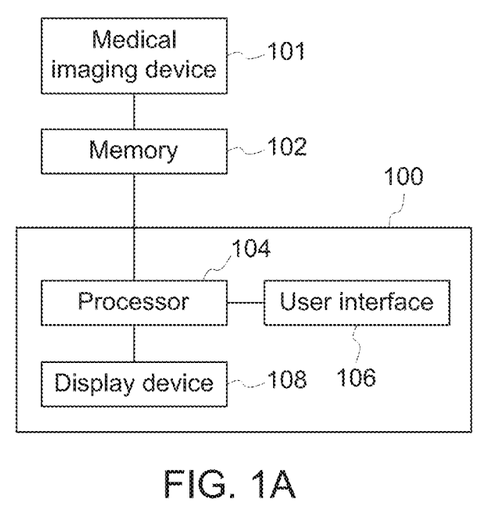
FIG. 1A is a schematic diagram of a system, a medical imaging device, and a memory in accordance with an embodiment.

FIG. 1A is a schematic diagram of a system 100, a medical imaging device 101, and a memory 102. The system 100 may be a workstation according to an exemplary embodiment. The system 100 is adapted for interacting with a 3D medical imaging dataset according to an embodiment. The system 100 includes a processor 104, a user interface 106, and a display device 108. The memory 102 may include any known medium for storing digital data, including, but not limited to a hard drive, a flash memory, random access memory (RAM), read only memory (ROM), a compact disc (CD), and a compact disc read-only memory (CD-ROM). The memory 102 may be part of a database, a component of a PACS/RIS system, or a stand-alone component. The medical imaging device 101 may comprise any type of medical imaging device capable of acquiring a 3D medical imaging dataset. For example, the medical imaging device 101 may be an ultrasound imaging system, a computed tomography (CT) imaging system, a magnetic resonance imaging (MRI) system, a nuclear medicine imaging system (SPECT), or a positron emission tomography (PET) imaging system according to various embodiments. The processor 104 is communicatively connected to the memory 102. This may be via either a wired or a wireless connection. The processor 104 may include one or more separate processing components. For example, the processor 104 may include a central processing unit (CPU), a microprocessor, a graphics processing unit (GPU), or any other electronic component capable of processing data according to specific logical instructions. Having a processor that includes a GPU may be advantageous for computation-intensive operations, such as volume-rendering large 3D medical imaging datasets. According to some embodiments, the memory 102 may be co-located with the processor 104. However, according to other embodiments, the memory 102 may be remotely located with respect to the processor 104 and accessed through technologies including wireless networks, the internet, or an intranet.

A user interface 106 is communicatively connected to the processor 104. The user interface 106 may be communicatively connected in either a wired or a wireless fashion. The user input 106 may include a trackball and one or more buttons according to an exemplary embodiment. However, according to other embodiments, the user interface 106 may include one or more of a mouse, a track pad, a touch screen, rotary controls, or an assortment of hard or soft keys with defined or definable functions. The display device 108 is communicatively connected to the processor 104 as well. The display device 108 may include a monitor or display screen such as a monitor, an LCD screen, an LED screen, a projector, or any other device suitable for displaying a volume-rendered image. Other embodiments may include multiple display devices.

Figure 1B:
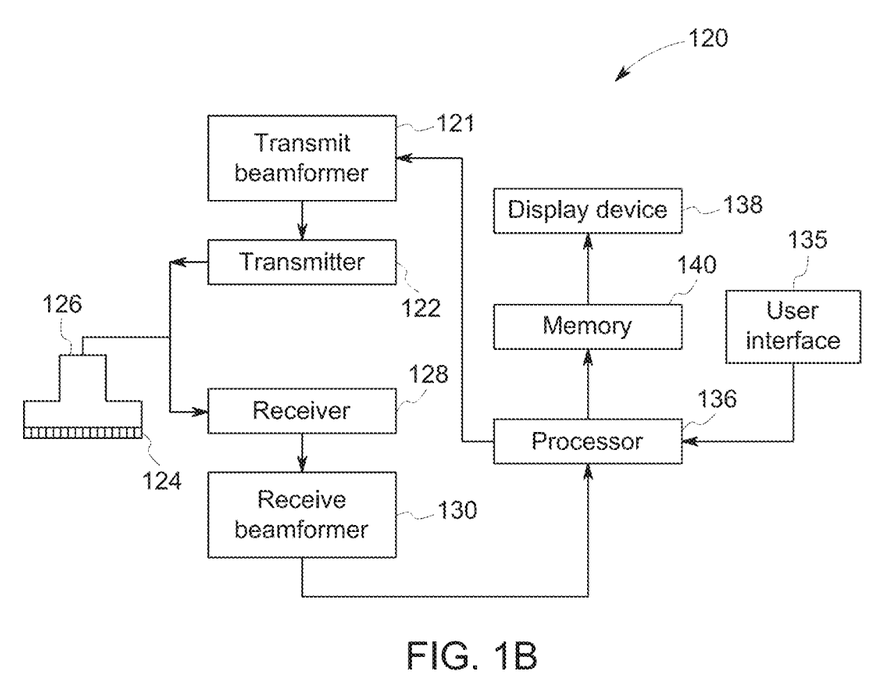
FIG. 1B is a schematic diagram of an ultrasound imaging system in accordance with an embodiment.

FIG. 1B is a schematic diagram of an ultrasound imaging system 120 in accordance with an embodiment. The ultrasound imaging system 120 includes a transmit beamformer 121 and a transmitter 122 that drive elements 124 within an ultrasound probe 126 to emit pulsed ultrasonic signals into a body (not shown). The ultrasound probe 126 may be a linear probe, a curved linear probe, a 2D array, a mechanical 3D/4D probe, or any other type of ultrasound probe capable of acquiring ultrasound data. Still referring to FIG. 1, the pulsed ultrasonic signals are back-scattered from structures in the body, like blood cells or muscular tissue, to produce echoes that return to the elements 124. The echoes are converted into electrical signals by the elements 124 and the electrical signals are received by a receiver 128. The electrical signals representing the received echoes are passed through a receive beamformer 130 that outputs ultrasound data. According to some embodiments, the ultrasound probe 126 may contain electronic circuitry to do all or part of the transmit and/or the receive beamforming. For example, all or part of the transmit beamformer 121, the transmitter 122, the receiver 128 and the receive beamformer 130 may be situated within the ultrasound probe 126. The terms "scan" or "scanning" may also be used in this disclosure to refer to acquiring data through the process of transmitting and receiving ultrasonic signals. A user interface 135 may be used to control operation of the ultrasound imaging system 120, including, to control the input of patient data, to set an acquisition preset, or to change a display parameter, and the like. The user interface 135 may include components such as a keyboard, a mouse, a track ball, a track pad, a touch screen, a multi-touch screen, and the like.

The ultrasound imaging system 120 also includes a processor 136 to control the transmit beamformer 121, the transmitter 122, the receiver 128 and the receive beamformer 130. The processor 136 is communicatively connected to the transmit beamformer 121, the transmitter 122, the receiver 128, and the receive beamformer 130 by either wired or wireless techniques. The processor 136 is in electronic communication with the ultrasound probe 126. The processor 136 may control the ultrasound probe 126 to acquire data. The processor 136 controls which of the elements 124 are active and the shape of a beam emitted from the ultrasound probe 126. The processor 136 is also in electronic communication with a display device 138, and the processor 136 may process the data into images or values for display on the display device 138. The display device 138 may comprise a monitor, an LED display, a cathode ray tube, a projector display, or any other type of apparatus configured for displaying an image. Additionally, the display device 138 may include one or more separate devices. For example, the display device 138 may include two or more monitors, LED displays, cathode ray tubes, projector displays, etc. The display device 138 may also be a touchscreen. For embodiments where the display device 138 is a touchscreen, the touchscreen may function as an input device and it may be configured to receive touch or touch gesture inputs from a user. For purposes of this disclosure, the term "electronic communication" may be defined to include both wired and wireless connections. The processor 136 may include a central processor (CPU) according to an embodiment. According to other embodiments, the processor 136 may include other electronic components capable of carrying out processing functions, such as a digital signal processor, a field-programmable gate array (FPGA), or a graphic board. According to other embodiments, the processor 136 may include multiple electronic components capable of carrying out processing functions. For example, the processor 136 may include two or more electronic components selected from a list of electronic components including: a central processor, a digital signal processor, an FPGA, and a graphic board. According to another embodiment, the processor 136 may also include a complex demodulator (not shown) that demodulates the RF data and generates raw data. In another embodiment the demodulation can be carried out earlier in the processing chain. The processor 136 may be adapted to perform one or more processing operations according to a plurality of selectable ultrasound modalities on the data. The data may be processed in real-time during a scanning session as the echo signals are received. For the purposes of this disclosure, the term "real-time" is defined to include a procedure that is performed without any intentional delay. For purposes of this disclosure, the term "real-time" will additionally be defined to include an action occurring within 2 seconds. For example, if data is acquired, a real-time display of that data would occur within 2 seconds of the acquisition. Those skilled in the art will appreciate that most real-time procedures/processes will be performed in substantially less time than 2 seconds. The data may be stored temporarily in a buffer (not shown) during a scanning session and processed in less than real-time in a live or off-line operation.

Some embodiments of the invention may include multiple processors (not shown) to handle the processing tasks. For example, a first processor may be utilized to demodulate and decimate the RF signal while a second processor may be used to further process the data prior to displaying an image. It should be appreciated that other embodiments may use a different arrangement of processors.

The ultrasound imaging system 120 may continuously acquire data at a given frame-rate or volume-rate. Images generated from the data may be refreshed at a similar frame-rate or volume-rate. A memory 140 is included for storing processed frames of acquired data. In an exemplary embodiment, the memory 140 is of sufficient capacity to store at least several seconds' worth of frames of ultrasound data. The frames of data are stored in a manner to facilitate retrieval thereof according to its order or time of acquisition. The memory 140 may comprise any known data storage medium.

Optionally, embodiments of the present invention may be implemented utilizing contrast agents. Contrast imaging generates enhanced images of anatomical structures and blood flow in a body when using ultrasound contrast agents including microbubbles. After acquiring data while using a contrast agent, the image analysis includes separating harmonic and linear components, enhancing the harmonic component and generating an ultrasound image by utilizing the enhanced harmonic component. Separation of harmonic components from the received signals is performed using suitable filters. The use of contrast agents for ultrasound imaging is well-known by those skilled in the art and will therefore not be described in further detail.

In various embodiments of the present invention, data may be processed by other or different mode-related modules by the processor 136 (e.g., B-mode, Color Doppler, M-mode, Color M-mode, spectral Doppler, Elastography, TVI, strain, strain rate, and the like) to form 2D or 3D data. For example, one or more modules may generate B-mode, color Doppler, M-mode, color M-mode, spectral Doppler, Elastography, TVI, strain, strain rate and combinations thereof, and the like. The image beams and/or frames are stored and timing information indicating a time at which the data was acquired in memory may be recorded. The modules may include, for example, a scan conversion module to perform scan conversion operations to convert the image frames from coordinates beam space to display space coordinates. A video processor module may be provided that reads the image frames from a memory and displays the image frames in real time while a procedure is being carried out on a patient. A video processor module may store the image frames in an image memory, from which the images are read and displayed.

Figure 2:
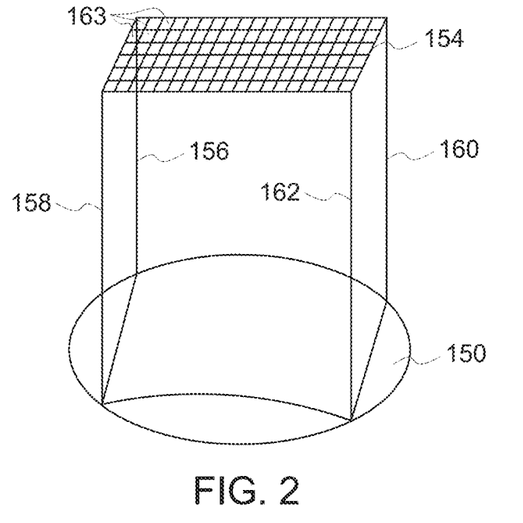
FIG. 2 is a schematic representation of a geometry that may be used to generate a volume-rendered image according to an embodiment.

FIG. 2 is a schematic representation of geometry that may be used to generate a volume-rendered image according to an embodiment. FIG. 2 includes a 3D medical imaging dataset 150 and a view plane 154.

Referring to both FIGS. 1A and 2, the processor 104 may generate a volume-rendered image according to a number of different techniques. According to an exemplary embodiment, the processor 104 may generate a volume-rendered image through a ray-casting technique from the view plane 154. The processor 104 may cast a plurality of parallel rays from the view plane 154 to or through the 3D medical imaging dataset 150. FIG. 2 shows a first ray 156, a second ray 158, a third ray 160, and a fourth ray 162 bounding the view plane 154. It should be appreciated that additional rays may be cast in order to assign values to all of the pixels 163 within the view plane 154. The 3D medical imaging dataset 150 may comprise voxel data, where each voxel, or volume-element, is assigned a value or intensity. Additionally, each voxel may be assigned an opacity as well. The value or intensity may be mapped to a color according to some embodiments. The processor 104 may use a "front-to-back" or a "back-to-front" technique for volume composition in order to assign a value to each pixel in the view plane 154 that is intersected by the ray. For example, starting at the front, that is the direction from which the image is viewed, the intensities of all the voxels along the corresponding ray may be summed. Then, optionally, the intensity may be multiplied by an opacity corresponding to the opacities of the voxels along the ray to generate an opacity-weighted value. These opacity-weighted values are then accumulated in a front-to-back or in a back-to-front direction along each of the rays. The process of accumulating values is repeated for each of the pixels 163 in the view plane 154 in order to generate a volume-rendered image. According to an embodiment, the pixel values from the view plane 154 may be displayed as the volume-rendered image. The volume-rendering algorithm may additionally be configured to use an opacity function providing a gradual transition from opacities of zero (completely transparent) to 1.0 (completely opaque). The volume-rendering algorithm may account for the opacities of the voxels along each of the rays when assigning a value to each of the pixels 163 in the view plane 154. For example, voxels with opacities close to 1.0 will block most of the contributions from voxels further along the ray, while voxels with opacities closer to zero will allow most of the contributions from voxels further along the ray. Additionally, when visualizing a surface, a thresholding operation may be performed where the opacities of voxels are reassigned based on the values. According to an exemplary thresholding operation, the opacities of voxels with values above the threshold may be set to 1.0 while voxels with the opacities of voxels with values below the threshold may be set to zero. Other types of thresholding schemes may also be used. An opacity function may be used to assign opacities other than zero and 1.0 to the voxels with values that are close to the threshold in a transition zone. This transition zone may be used to reduce artifacts that may occur when using a simple binary thresholding algorithm. For example, a linear function mapping opacities to values may be used to assign opacities to voxels with values in the transition zone. Other types of functions that progress from zero to 1.0 may also be used. Volume-rendering techniques other than the ones described above may also be used in order to generate a volume-rendered image from a 3D medical imaging dataset.

The volume-rendered image may be shaded and illuminated in order to present the user with a better perception of depth of the rendered object represented in the volume-rendered image. This may be performed in several different ways according to various embodiments. For example, a surface of a rendered object may be defined based on the volume-rendering of the 3D medical imaging dataset. According to an exemplary embodiment, a gradient may be calculated at each of the pixels. The processor 104 (shown in FIG. 1) may compute the amount of light at positions corresponding to each of the pixels and apply standard shading methods based on the gradients and specific light directions. The view direction may correspond with the view direction shown in FIG. 2. The processor 104 may also use multiple virtual light sources as inputs when generating the volume-rendered image. For example, when ray casting, the processor 104 may calculate how much light is reflected, scattered, or transmitted from each voxel in a particular view direction along each ray. This may involve summing contributions from multiple virtual light sources. The processor 104 may calculate the contributions from all the voxels in the volume. The processor 104 may calculate composite values from all of the voxels, or interpolated values from neighboring voxels, in order to compute the final value of the displayed pixel on the image. While the aforementioned example described an embodiment where the voxel values are integrated along rays, volume-rendered images may also be calculated according to other techniques such as using the highest value along each ray, using a lowest value along each ray, using an average value along each ray, or using any other volume-rendering technique.

Figure 3:
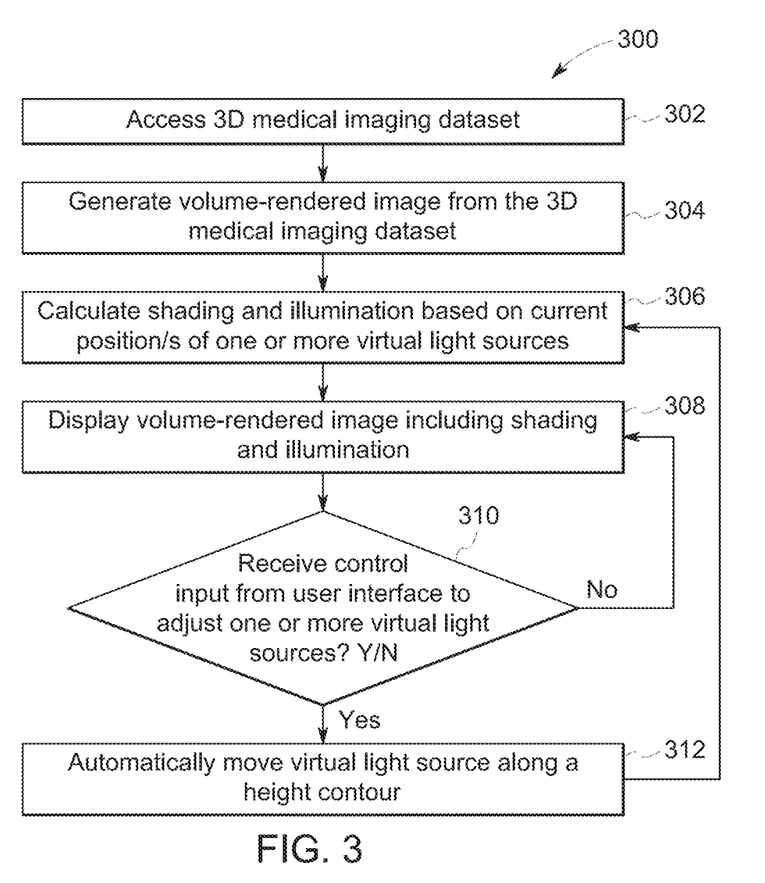
FIG. 3 is a flow chart of a method 300 in accordance with an embodiment.

FIG. 3 is a flow chart of a method 300 in accordance with an embodiment. According to exemplary embodiments, the method 300 may be performed with the system 100 shown in FIG. 1A or the ultrasound imaging system 100 shown in FIG. 1B. The technical effect of the method 300 adjustment of the virtual light source to an updated position along a height contour established with respect to a surface of a rendered object in a volume-rendered image. FIG. 3 will be described according to an exemplary embodiment where the method 300 is performed with the system 100 shown in FIG. 1A.

Referring to FIGS. 1A and 3, the medical imaging device 101 acquires a three-dimensional (3D) medical imaging dataset and stores the medical imaging dataset in the memory 102. At step 302, the processor 104 accesses the 3D medical imaging dataset from a memory such as the memory 102.

The 3D medical imaging dataset may include voxel data where each voxel is assigned a value and an opacity. The value and opacity may correspond to the intensity of the voxel. At step 304, the processor 104 generates a volume-rendered image from the 3D medical imaging dataset. According to an embodiment, the processor 104 may generate the volume-rendered image according to one of the techniques previously described with respect to FIG. 2. At step 306, the processor 104 determines the shading and illumination for the volume-rendered image. As described hereinabove with respect to FIG. 2, the shading of the volume-rendered image may include calculating how light from one or more virtual light sources would interact with the structures of the the rendered object represented in the volume-rendered image. The method 300 will be described according to an exemplary embodiment where the shading and illumination of the volume-rendered image is calculated using a single virtual light source, but it should be appreciated that in other embodiments, the processor 104 may be configured to calculate the shading and illumination based on two or more virtual light sources. The algorithm controlling the shading may calculate how the light would reflect, refract, and diffuse based on intensities, opacities, and gradients in the 3D medical imaging dataset. The intensities, opacities, and gradients in the 3D medical imaging dataset may correspond with tissues, organs, and structures in the volume-of-interest from which the 3D medical imaging dataset was acquired. At step 306, the processor 104 calculates the shading and the illumination of the volume-rendered image based on the current, or real-time, position of the virtual light source or the current positions of multiple virtual light sources. According to an example, the processor 104 may calculate the shading and illumination at step 306 based on the assumption that each virtual light source acts as a point source. According to other examples, the processor 104 may calculate the shading and illumination at step 306 based on the assumption that each virtual light source is a is not a point source. For example, the processor 104 may calculate the shading and the illumination of the volume-rendered image based on the assumption that each virtual light source is a sphere or other geometrical shape.

At step 308, the processor 104 is configured to display the volume-rendered image including the shading and the illumination calculated at step 308 on the display device 108. The position of the virtual light source will therefore directly affect the appearance of the volume-rendered image displayed on the display device 108.

Step 310 is a decision step in the method 300. If the processor 104 does not receive a control input from the user interface at step 310, then the method 300 returns to step 308 and the volume-rendered image with the previously calculated illumination and shading is displayed. If, however, at step 310, the processor 104 receives a control input from the user interface 106 to adjust the position of one or more of the virtual light sources, then the method 300 advances to step 312.

At step 312, the processor 106 automatically moves the virtual light source along a height contour in response to the control input. The height contour is calculated by the processor 106 at a generally fixed distance from a surface, such as the outer surface 407 of the rendered object 403 represented in the volume-rendered image 402. According to an example, the height contour may be at a constant height with respect to the outer surface 407 of the rendered object in the volume-rendered image. According to another example, the height contour may be at a constant height with respect to a smoothed surface of the volume-rendered image 407. The processor 106 may, for instance, apply a smoothing function to the outer surface of the rendered object represented in the volume-rendered image and then calculate the height contour that is a constant height with respect to the smoothed surface. The smoothing function may include an averaging function, a curve-fitting function, or a moving-average function for instance.

The height contour is determined by the processor 106 to be either a fixed distance (height) from the outer surface of the rendered object in the volume-rendered image or to be a generally fixed distance (height) from the outer surface of the rendered object in the volume-rendered image. The height of the height contour may be manually adjusted by the user. According to an example, the user may use a rotary control to adjust a height of the height contour from the surface of the rendered object in the volume-rendered image. According to another example, the user may use slider or a virtual slide bar to adjust the height of the height contour from the surface of the rendered object or objects in the volume-rendered image. The height contour may be positioned at a positive height above the surface of the rendered object, the height contour may be positioned at a negative height below the surface of the rendered object, or the height contour may be positioned exactly at the surface of the rendered object. For convention, in this disclosure, a height of zero will be defined to be at exactly at the surface of the rendered object, a positive height will be defined to be in a direction away from a center of the rendered object from the surface, and a negative height will be defined to be in a direction towards the center of the rendered object from the surface. In response to an input entered through the user interface 106, the processor 104 may therefore adjust a height of the virtual contour.

After implementing step 312, the method 300 returns to step 306 where the processor 106 calculates the shading and illumination for the volume-rendered image based on the updated position of the virtual light source. Or for examples using multiple light sources, the processor 106 calculates the shading and illumination for the volume-rendered image based on the current, or real-time, position of multiple virtual light sources, one or more of which may be an updated position.

Figure 4:
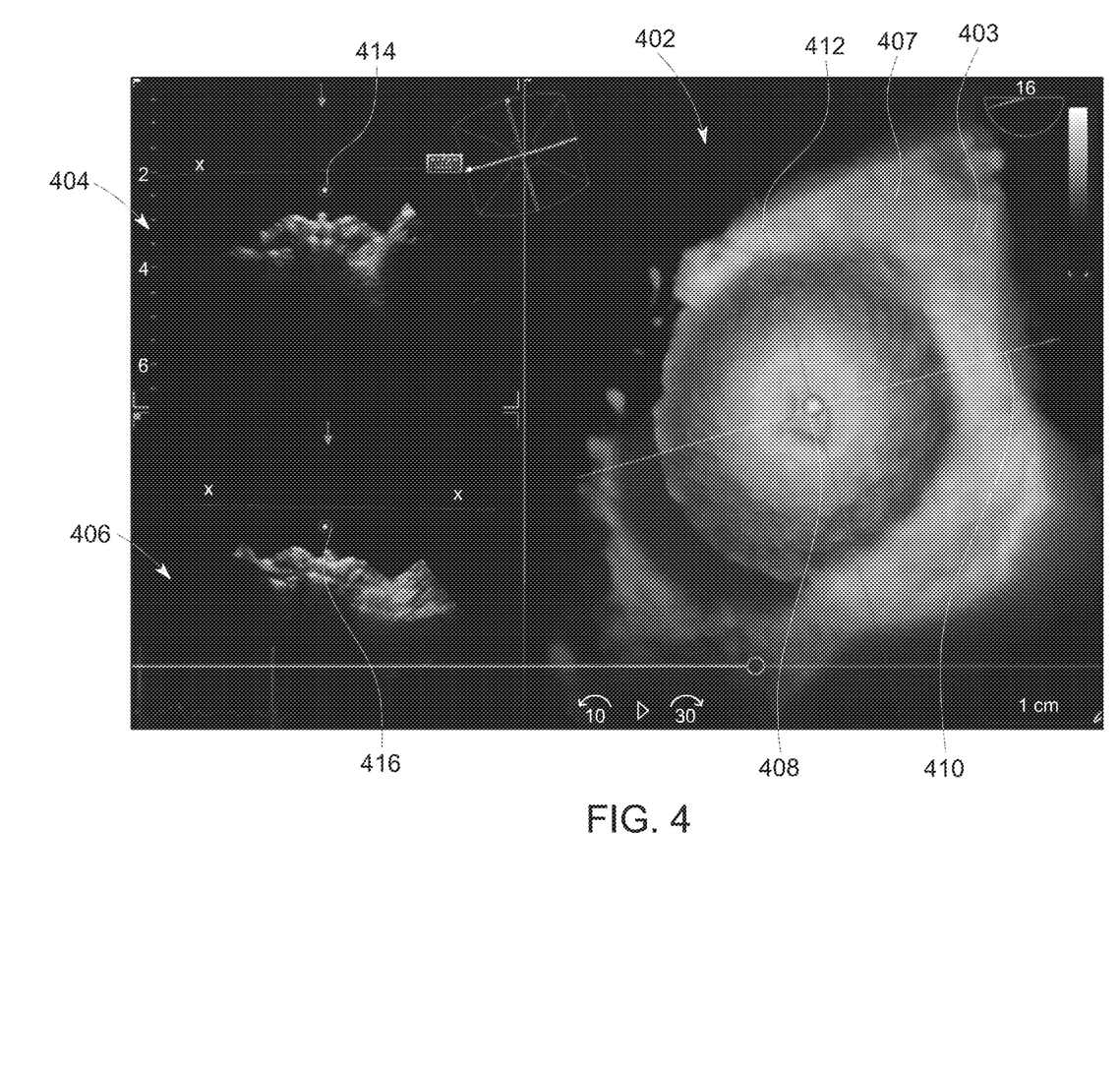
FIG. 4 is a representation of a screen shot at a first time in accordance with an embodiment.

FIG. 4 is a representation of a screen shot at a first time in accordance with an embodiment. The screen shot includes a volume-rendered image 402, a first reference plane 404, and a second reference plane 406. The volume-rendered image 402 includes a rendered object 403. The rendered object 403 may include one or more anatomical structures and or objects represented in the 3D medical imaging dataset. The rendered object 403 includes an outer surface 407. The outer surface 407 defines the volume of the rendered object 403 represented in the volume-rendered image. The first reference plane 404 represents a planar view through the volume-rendered image 402 along line 410. The second reference plane represents a planar view through the volume rendered image along line 412. FIG. 4 also includes a light source indicator 408, a first reference plane light source indicator 414 and a second reference plane light source indicator 416. The volume-rendered image 402, may be generated from a 3D medical imaging dataset as described in step 304 of the method 300. The volume-rendered image 402 includes shading and illumination based on a current, or real-time, position of a virtual light source as described in step 306 of the method 300. The position of the virtual light source is represented by the light source indicator 408, which is shown in the volume-rendered image 402 in the geometrical relationship that was used to calculate the illumination and shading in the volume-rendered image 402. FIG. 4 is a representation of the screen shot at a first time.

Figure 5:
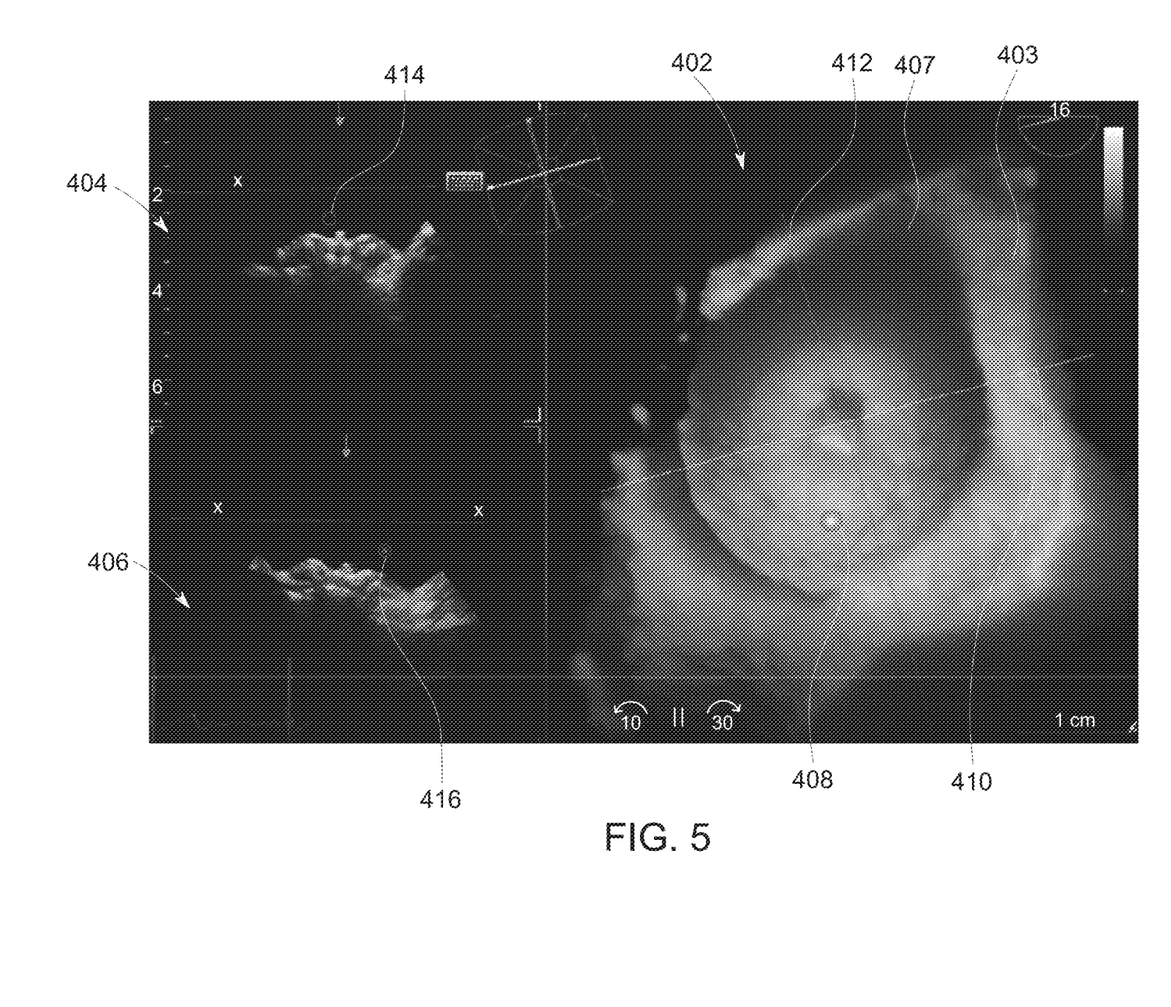
FIG. 5 is representation of a screen shot at a second time in accordance with an embodiment.

FIG. 5 is a representation of a screen shot at a second time in accordance with an embodiment. The light source indicator 408 is in a different position in FIG. 5 compared to FIG. 4 indicating that the position of the virtual light source is different in FIG. 5 compared to FIG. 4.

Figure 6:
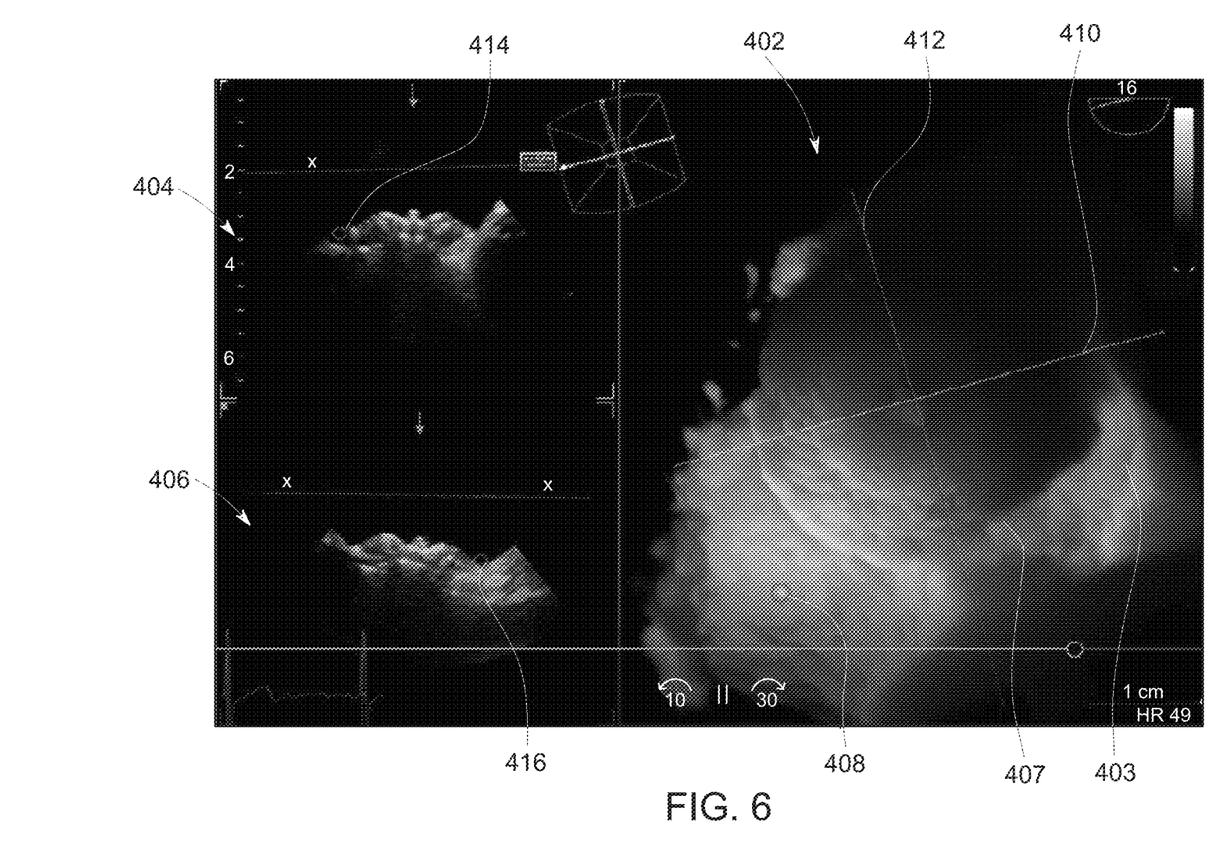
FIG. 6 is a representation of a screen shot at a third time in accordance with an embodiment.

FIG. 6 is a representation of a screen shot at a third time in accordance with an embodiment. The light source indicator 408 is in a different position in FIG. 6 compared to FIGS. 4 and 5, which indicates that the position of the virtual light source is different in FIG. 6 compared to FIGS. 4 and 5.

Figure 7:
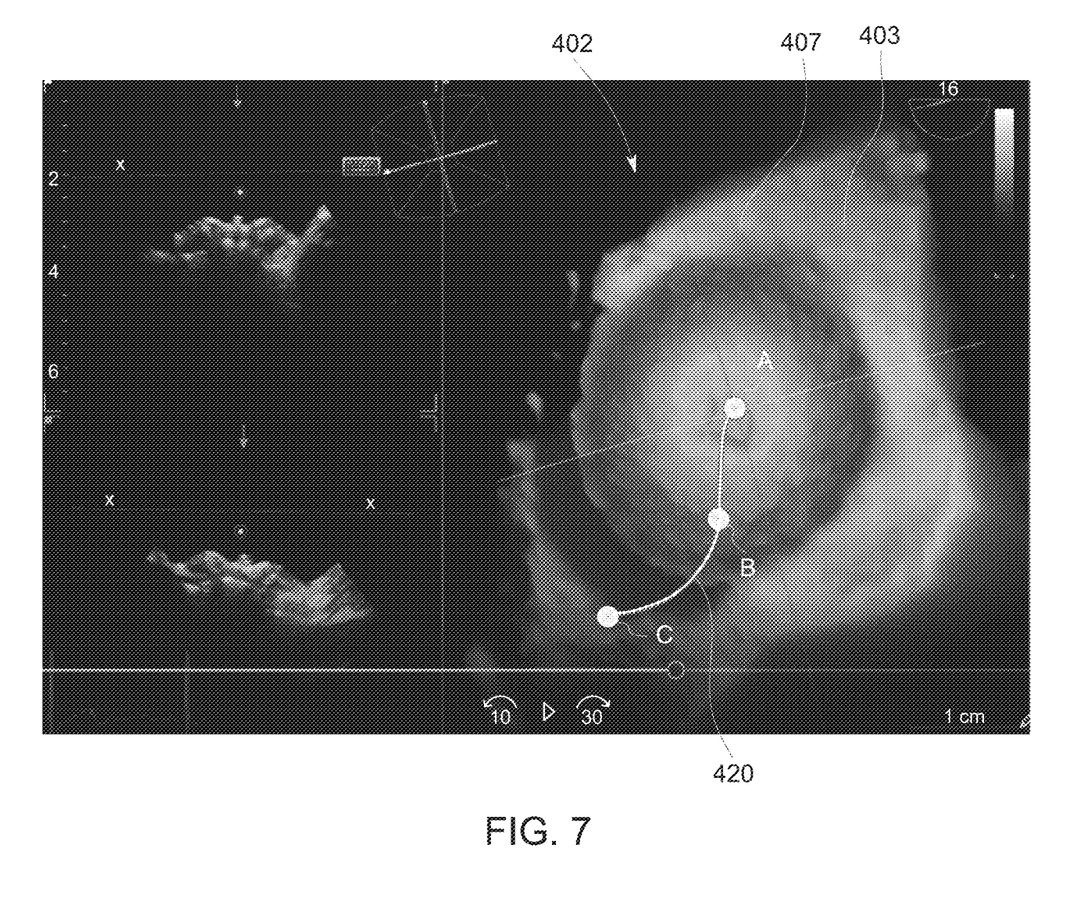
FIG. 7 is a representation of a screen shot and an overlay showing an exemplary path of a light source indicator in accordance with an embodiment.

FIG. 7 is a representation of a screen shot and an overlay showing an exemplary path 420 of the light source indicator 408 in accordance with an embodiment. The light source indicator 408 is at point A on the path 420 in the volume-rendered image 402 shown in FIG. 4; the light source indicator 408 is at point B on the path 420 in the volume-rendered image 402 shown in FIG. 5; and the light source indicator 408 is at point C on the path 420 in the volume-rendered image 402 shown in FIG. 6. The light source indicator 408 provides a representation of the relative positioning between the virtual light source used to calculate the illumination and shading of the volume-rendered image 402 at the first time shown in FIG. 4, the second time shown in FIG. 5, and the third time shown in FIG. 6. The light source indicator 408 travels along the path 420 from point A to point B between the first time and the second time; and the light source indicator 408 travels along the path 420 from point B to point C between the second time and the third time. It should be appreciated that the path 420 represents an exemplary path and that an operator could control the light source indicator to follow other paths by varying the control input or inputs entered through the user interface 106.

According to an embodiment, the control input that is optionally received at step 310 may be a control received from a mouse, a control input received from a trackball, or a control input received from a touchscreen or a touchpad. The control input or inputs may optionally trace the path 420 shown in FIG. 7. For example, the operator may input a control input on a touchscreen or a touchpad that is the same shape or a similar shape as the path 420 shown on FIG. 7. Likewise, for embodiments using a mouse or a trackpad, a control input may be received where the mouse or trackball defines a curve with either the same shape as the path 420 or a very similar shape as the path 420.

According to an embodiment, the user may define a height of a height contour used to define the height of the virtual light source with respect to the surface shown in the volume-rendered image. The user may for instance, adjust a height of the virtual light source using a rotary, a slide bar, a manual increment/decrement controller, or any other type or user interface control. The user may for instance, control the height of the virtual light source with the user interface 106 and the processor 104 may optionally show the height of the virtual light source above the surface of the volume-rendered image 402. The processor 104 may optionally display the height of the virtual light source on the display device 108 in millimeters (mm), centimeters (cm), or inches.

According to an embodiment, at step 312, the processor 104 automatically moves the virtual light source along a height contour that is a either a constant height from a surface of the volume-rendered image 402 or that is a constant height from a smoothed surface 407 of the volume-rendered image 402. The height of the height contour may be determined in a direction perpendicular to the outer surface of the volume-rendered image 402 for instance. The processor 104 receives a control input at step 310 to adjust a position of one or more virtual light sources. As described previously, this may, for example, be an input through a mouse, a trackball, a touchscreen, or a touchpad. Upon receiving this control input at step 310, the processor 104 automatically moves the virtual light source along the height contour. Until a separate height control adjustment input is received through the user interface 106, the processor 104 automatically maintains the virtual light source along the height contour as the method 300 repeats steps 306, 308, 310, and 312 and additional control inputs are received. The permits the user to easily position the virtual light source at any position with respect to the rendered object shown in the volume-rendered image 402 while maintaining the virtual light source at a fixed height from a surface, such as the outer surface 407, of the rendered object 403. Advantageously, the technique described with respect to the method 300 allows the user to easily control the position of the virtual light source in three-dimensions using only a two-dimensional control input. The processor 104 automatically keeps the virtual light source at a generally constant height, defined by the height contour, from the surface of the rendered object 403. This makes it much easier and quicker for the clinician to reposition the virtual light source to a different location while keeping the virtual light source at a generally constant distance from the surface of the rendered object 403. Keeping the virtual light source at a generally constant distance helps ensure relatively similar intensity levels from the virtual lighting source at different positions. Additionally, keeping the virtual light source at a generally constant distance help ensure that the illumination, shading, and any shadows cast from structures of the rendered object will vary smoothly as the position of the virtual light source is adjusted.

The path 420 shown in FIG. 7 represents the path of the light source indicator 408 according to an embodiment. The path 420 is a graphical way to represent the position of the virtual light source indicator used to determine the illumination and shading of the volume-rendered image 402. At the first time represented in FIG. 4, the light source indicator 408 is at position A. At the second time represented in FIG. 5, the light source indicator 408 is at position B. At the third time represented in FIG. 5, the light source indicator 408 is at position C. Since the light source indicator 408 represents the position of the virtual light source with respect to the rendered object 403 in the volume-rendered image 402, the processor 104 automatically moves the virtual light source along a height contour from the first time, to the second time and to the third time. The path 420, which shows the path of the light source indicator, represents the path of the virtual light source from the first time, to the second time, to the third time. The processor 104 controls the virtual light source to be at a constant height with respect to the outer surface of the rendered object shown in the volume-rendered image 402.

According to an embodiment, the processor 104 may also be used to control a reference plane light source indicator, such as the either the first reference plane light source indicator 414 or the second reference plane light source indicator 416. The processor 104 may be configured to control one or more display properties of each reference plane light source indicator to indicate the distance of the virtual light source from the plane represented in the reference plane. For example, the processor 104 may use intensity, color, size of the reference plane light source indicator, or a combination or intensity, color, and size to indicate the distance of the virtual light source from the plane represented in a particular reference plane. FIGS. 4, 5, and 6 will be used to help describe how the reference plane light source indicators function according to an embodiment.

As previously described, the first reference plane 404 represents a first plane along line 410 and the second reference plane 406 represents a second plane along line 412. According to the embodiment shown in FIGS. 4, 5, and 6, the first plane and the second plane may be perpendicular to each other. At the first time, shown in FIG. 4, the light source indicator 408 is positioned almost exactly where the line 410 and line 412 cross. The first reference plane light source indicator 414 represents the position of the virtual light source with respect to the first reference plane 404. The second reference plane light source indicator 416 represents the position of the virtual light source with respect to the second reference plane 406.

At the second time, represented in FIG. 5, the light source indicator 408 is not positioned on either the line 410 or the line 412. This means that the virtual light source is not positioned in either the first plane or the second plane. As such processor 104 adjusts the display of the first reference plane light source indicator 414 and the second reference plane light source indicator 416. For example, the processor 104 may control the intensity of either reference plane light source indicator to indicate the position of the virtual light source with respect to the reference plane. For example, the virtual light source is relatively far from the first plane, indicated by line 410. The first reference plane light source indicator 414 is shown as a ring with a dark central portion. According to an embodiment, this indicates that the virtual light source is relatively far from the first plane. The virtual light source is relatively closer to the second plane, indicated by the second line 412. As such, the second reference plane light source indicator 416 is brighter than the first reference plane light source indicator 414 in FIG. 5. Both the first reference plane light source indicator 414 and the second reference plane light source indicator 416 shown in FIG. 4 have a brighter intensity than the first reference plane light source indicator 414 and the second reference plane light source indicator 416 shown in FIG. 5. This is because at the first time, indicated in FIG. 4, the first reference plane light source indicator 414 is located in the first plane and the second reference plane light source indicator 416 is located in the second plane. In FIG. 6, representing a third time, the virtual light source is approximately equally far away from both the first plane and the second plane as shown by the position of the light source indicator 408 with respect to the first line 410 and the second line 412. The processor 104 therefore displays the first reference plane light source indicator 414 and the second reference plane light source indicator 416 at with the same intensity. The intensities of both the first reference plane light source indicator 414 and the second reference plane light source indicator 416 are relatively low to indicate that the virtual light source is positioned relatively far from both the first plane and the second plane.

In the example described with respect to FIGS. 4, 5, and 6 the processor 104 adjusts the intensity of each reference plane light source indicator to indicate the distance of the virtual light source from the plane represented in the reference plane. According to an embodiment, the processor 104 may be configured to control the reference plane light source indicator to be at a maximum intensity when the virtual light source is in the reference plane and at less than a maximum intensity when the virtual light source is not in the reference plane. In FIG. 4, the reference plane light source indicator may be adjusted to represent the distance of the virtual light source from the plane represented in the reference plane.

Figure 8:
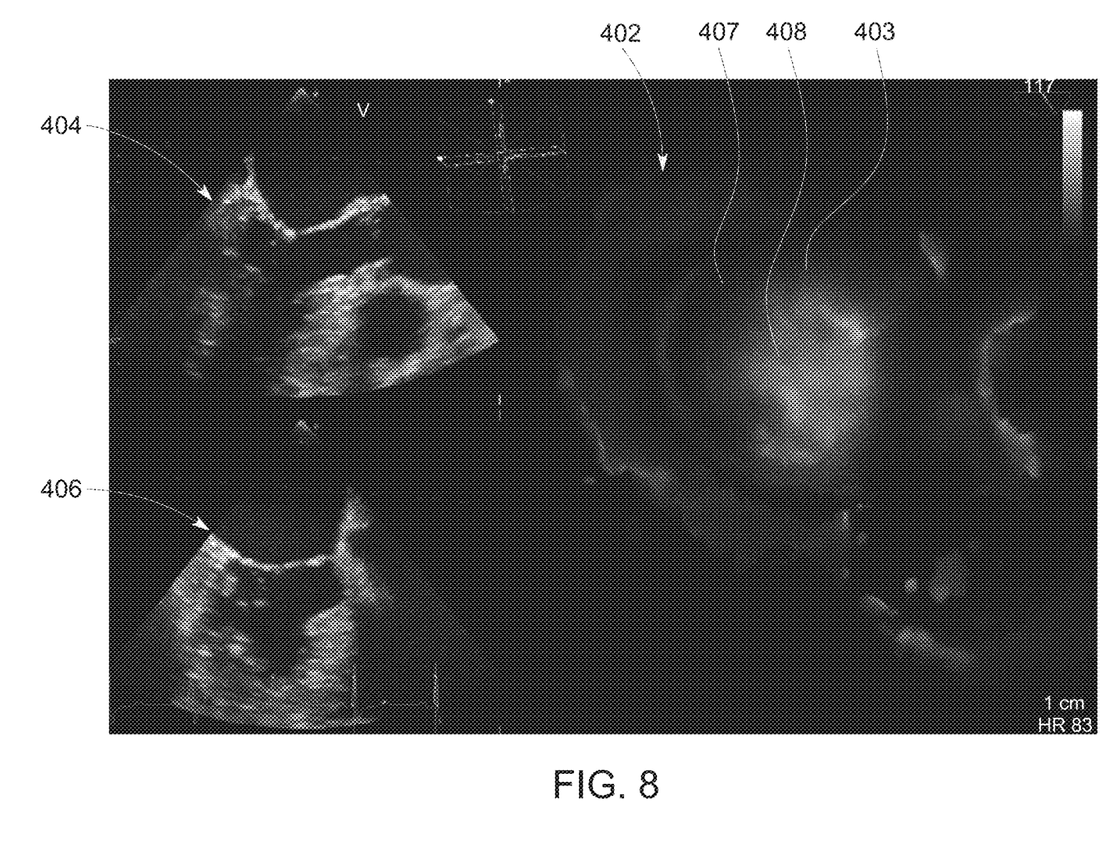
FIG. 8 is representation of a screen shot in accordance with an embodiment.

FIG. 8 is a representation of screen shot according to an embodiment. FIG. 8 shows an example where the virtual light source is positioned below the outer surface of the rendered object in the volume-rendered image 402. The volume-rendered image 402 is backlit since the virtual light source is positioned below the outer surface of the rendered object. The height contour for the example shown in FIG. 8 is below the surface (or in a negative direction from the surface). In response to receiving a user input to adjust a position of the virtual light source, the processor 104 will cause the virtual light source to follow the height contour at a fixed negative distance from the outer surface of the rendered object 403.

Figure 9:
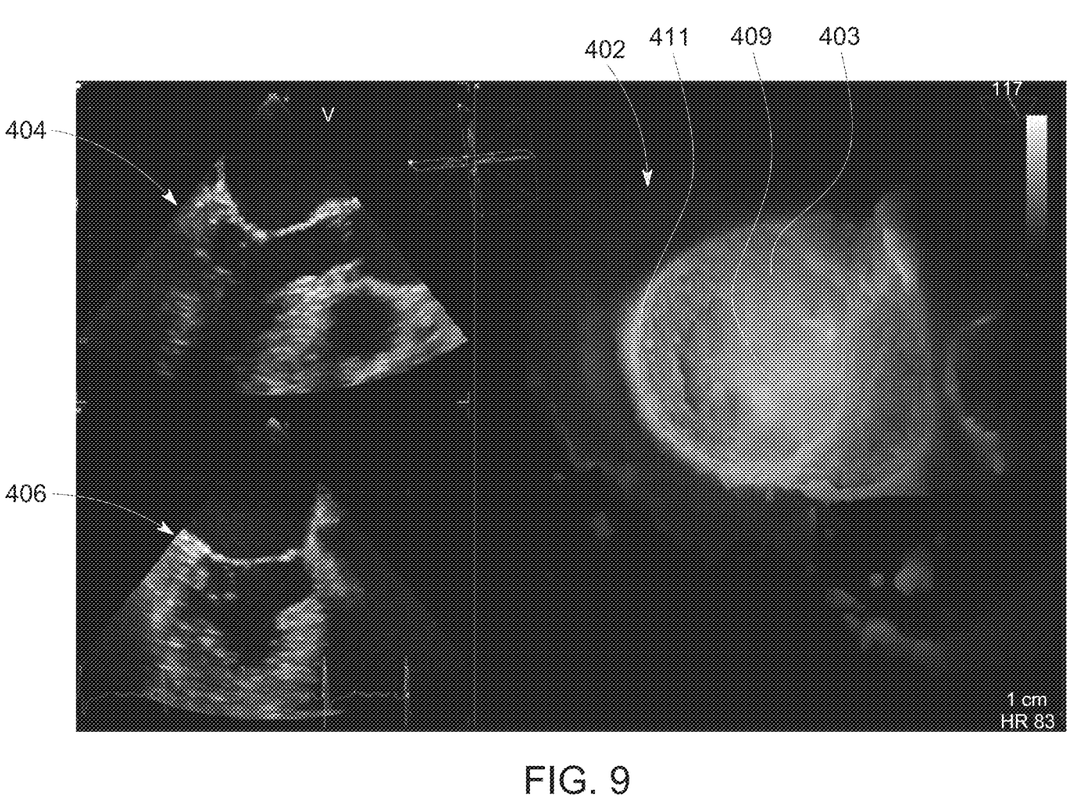
FIG. 9 is representation of a screen shot in accordance with an embodiment.

FIG. 9 is a representation of a screen shot according to an embodiment. FIG. 9 shows an example of an embodiment with two virtual light sources: a first virtual light source and a second virtual light source. The first virtual light source is represented by a first light source indicator 409 and the second virtual light source is represented by a second light source indicator 411.

According to an embodiment, the user may select to control the position of either virtual light source independently or the user may move both of the virtual light sources based on a single user input. According to an exemplary embodiment, the user may select one of the virtual light sources, such as by clicking on or selecting either the first light source indicator 409 or the second light source indicator 411. Then, the user may adjust the position of the selected virtual light source based according to the technique described with respect to the method 300.

In the example shown in FIG. 9, the first virtual light source is positioned beneath the outer surface of the rendered object as indicated by the first light source indicator 409, and the second virtual light source is positioned above the outer surface of the rendered object 403 as indicated by the second light source indicator 411. According to the embodiment shown in FIG. 9, the second light source indicator 411 is shown with a greater intensity than the first light source indicator 409 to indicate that the second virtual light source is above the outer surface and the first virtual light source is located below the outer surface of the rendered object. According to the embodiment, shown in FIG. 9, the second light source indicator 411 is larger in size than the first light source indicator 409. The processor 104 may adjust the size of each light source indicator based on a height of the light source indicator with respect to a surface of the rendered object 403. According to the embodiment shown in FIG. 9, the processor 104 may be configured to display the light source indicator as larger in size when the virtual light source is above the surface of the rendered object and as smaller in size when the virtual light source is below the surface of the rendered object. The processor 104 may be configured to smoothly vary the size of the light source indicator, such as either the first light source indicator 409 or the second light source indicator 411, as the user adjusts the height of the associated virtual light source. In this way, the size of the light source indicator may convey information about the height of the virtual light source with respect to a surface in the rendered object 104.

This written description uses examples to disclose the invention, including the best mode, and also to enable any person skilled in the art to practice the invention, including making and using any devices or systems and performing any incorporated methods. The patentable scope of the invention is defined by the claims, and may include other examples that occur to those skilled in the art. Such other examples are intended to be within the scope of the claims if they have structural elements that do not differ from the literal language of the claims, or if they include equivalent structural elements with insubstantial differences from the literal language of the claims.

I claim:

1. A method of volume-rendering comprising:
   accessing a 3D medical imaging dataset;
   generating a volume-rendered image including a rendered object from the 3D medical imaging dataset; and
   controlling a shading and an illumination of the volume-rendered image based on a position of a virtual light source with respect to the rendered object, wherein controlling the shading and the illumination comprises performing the following steps:
   a) receiving a control input from a user interface;
   b) automatically moving the virtual light source to an updated position along a height contour established with respect to a surface of the rendered object in the volume-rendered image in response to the control input, wherein the height contour is established to permit the virtual light source to be positioned at any position with respect to the rendered object while maintaining the virtual light source at a constant height with respect to either the surface of the rendered object or a smoothed surface of the rendered object;
   c) calculating an updated shading and an updated illumination based on the updated virtual light source position;
   d) displaying the volume-rendered image with the updated shading the updated illumination; and
   e) repeating steps a), b), c), and d) as the virtual light source is being moved in response to the control input.

2. The method of claim 1, wherein the height contour is at a constant height with respect to the surface of the rendered object.

3. The method of claim 1, wherein the height contour is at a constant height with respect to the smoothed surface of the rendered object, and wherein the smoothed surface is determined by applying a smoothing function to the surface of the rendered object.

4. The method of claim 1, further comprising adjusting a height of the height contour with respect to the surface of the rendered object in response to a second control input on the user interface.

5. The method of claim 1, wherein the height contour is above the surface of the rendered object.

6. The method of claim 1, wherein the height contour is below the surface of the rendered object.

7. The method of claim 1, wherein said controlling the shading and the illumination of the volume-rendered image is further based on a second virtual light source.

8. The method of claim 7, wherein the second virtual light source is positioned below the surface of the rendered object and the virtual light source is positioned above the surface of the rendered object.

9. The method of claim 1, further comprising displaying a light source indicator on the volume-rendered image to indicate the position of the virtual light source with respect to the rendered object.

10. The method of claim 9, further comprising displaying a reference plane with a reference plane light source indicator at the same time as the volume-rendered image, wherein the reference plane light source indicator indicates the position of the virtual light source with respect to the reference plane.

11. The method of claim 10, further comprising adjusting an intensity of the reference plane light source indicator to indicate the position of the virtual light source with respect to the reference plane.

12. The method of claim 11, wherein the reference plane light source indicator is displayed at a maximum intensity when it is in the reference plane, and wherein the reference plane light source indicator is displayed at less than maximum intensity when it is not in the reference plane.

13. The method of claim 12, wherein the intensity of the reference plane light source indicator is adjusted as the virtual light source is moved to indicate a distance of the virtual light source from the reference plane.

14. A system for interacting with a 3D medical imaging dataset comprising:
a display device;
a user interface; and
a processor communicatively connected to the display device and the user interface,
wherein the processor is configured to:
access a 3D medical imaging dataset;
generate a volume-rendered image including a rendered object from the 3D medical imaging dataset;
receive a control input from the user interface to adjust a position of a virtual light source with respect to the rendered object, wherein the position of the virtual light source is used to calculate an illumination and a shading of the volume-rendered image;
automatically move the virtual light source to an updated position along a height contour established with respect to a surface of the rendered object in the volume-rendered image in response to the control input, wherein the height contour is established to permit the virtual light source to be positioned at any position with respect to the rendered object while maintaining the virtual light source at a constant height with respect to either the surface of the rendered object or a smoothed surface of the rendered object; and
display the volume-rendered image with the illumination and the shading determined based on a real-time position of the virtual light source during the process of automatically moving the virtual light source to the updated position.

15. The system of claim 14, wherein the height contour is at a constant height with respect to the smoothed surface of the rendered object.

16. The system of claim 14, wherein the processor is configured to receive a second control input to add a second virtual light source, and wherein the processor is configured to display the volume-rendered image with the illumination and shading determined based on the real-time position of the virtual light source and the second virtual light source.

17. The system of claim 14, wherein the processor is configured to display a reference plane with a reference plane light source indicator at the same time as the volume-rendered image, wherein reference plane light source indicator indicates the position of the virtual light source with respect to the reference plane.

18. An ultrasound imaging system comprising:
an ultrasound probe;
a display device;
a memory;
a user interface; and
a processor communicatively connected to the ultrasound probe, the display device, the memory, and the user interface, wherein the processor is configured to:
control the ultrasound probe to acquire a 3D ultrasound dataset;
generate a volume-rendered image including a rendered object from the 3D ultrasound dataset;
receive a control input from the user interface to adjust a position of a virtual light source with respect to the rendered object, wherein the position of the virtual light source is used to calculate an illumination and a shading of the volume-rendered image;
automatically move the virtual light source to an updated position along a height contour established with respect to a surface of the rendered object in the volume-rendered image in response to the control input, wherein the height contour is established to permit the virtual light source to be positioned at any position with respect to the rendered object while maintaining the virtual light source at a constant height with respect to either the surface of the rendered object or a smoothed surface of the rendered object; and
display the volume-rendered image with the illumination and the shading determined based on a real-time position of the virtual light source during the process of automatically moving the virtual light source to the updated position.

19. The ultrasound imaging system of claim 18, wherein the height contour is at a constant height with respect to the surface of the volume-rendered image.

20. The ultrasound imaging system of claim 18, wherein the height contour is at a constant height with respect to the smoothed surface of the volume-rendered image, and wherein the smoothed surface is determined by applying a smoothing function to the surface of the volume-rendered image.

* * * * *